US009572859B2

(12) United States Patent
Hughes et al.

(10) Patent No.: US 9,572,859 B2
(45) Date of Patent: Feb. 21, 2017

(54) COMPOSITIONS AND METHODS FOR LOCALIZED THERAPY OF THE EYE

(71) Applicant: ALLERGAN, INC., Irvine, CA (US)

(72) Inventors: Patrick M. Hughes, Aliso Viejo, CA (US); Orest Olejnik, Coto de Caza, CA (US); Scott M. Whitcup, Laguna Hills, CA (US); James A. Burke, Santa Ana, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/857,707

(22) Filed: Apr. 5, 2013

(65) Prior Publication Data

US 2014/0031298 A1 Jan. 30, 2014

Related U.S. Application Data

(63) Continuation of application No. 13/367,070, filed on Feb. 6, 2012, which is a continuation of application No. 11/039,192, filed on Jan. 19, 2005, now abandoned.

(60) Provisional application No. 60/537,620, filed on Jan. 20, 2004.

(51) Int. Cl.
*A61K 9/00* (2006.01)
*A61K 38/13* (2006.01)
*A61K 47/36* (2006.01)
*A61K 31/00* (2006.01)
*A61K 9/14* (2006.01)
*A61K 9/10* (2006.01)

(52) U.S. Cl.
CPC ............ *A61K 38/13* (2013.01); *A61K 9/0048* (2013.01); *A61K 9/0051* (2013.01); *A61K 31/00* (2013.01); *A61K 47/36* (2013.01); *A61K 9/10* (2013.01); *A61K 9/14* (2013.01); *Y10S 514/912* (2013.01)

(58) Field of Classification Search
None
See application file for complete search history.

(56) References Cited

U.S. PATENT DOCUMENTS

| | | | |
|---|---|---|---|
| 3,396,081 A | 8/1968 | Billek et al. |
| 3,845,770 A | 11/1974 | Theeuwes et al. |
| 3,916,899 A | 11/1975 | Theeuwes et al. |
| 4,008,864 A | 2/1977 | Torphammar et al. |
| 4,014,335 A | 3/1977 | Arnold |
| 4,052,505 A | 10/1977 | Higuchi et al. |
| 4,057,619 A | 11/1977 | Higuchi et al. |
| 4,063,064 A | 12/1977 | Saunders et al. |
| 4,088,864 A | 5/1978 | Theeuwes et al. |
| 4,144,317 A | 3/1979 | Higuchi et al. |
| 4,158,005 A | 6/1979 | Bodor et al. |
| 4,186,184 A | 1/1980 | Zaffaroni |
| 4,190,642 A | 2/1980 | Gale et al. |
| 4,200,098 A | 4/1980 | Ayer et al. |
| 4,281,654 A | 8/1981 | Shell et al. |
| 4,285,987 A | 8/1981 | Ayer et al. |
| 4,303,637 A | 12/1981 | Shell et al. |
| 4,304,765 A | 12/1981 | Shell et al. |
| 4,327,725 A | 5/1982 | Cortese |
| 4,383,992 A | 5/1983 | Lipari |
| 4,396,625 A | 8/1983 | Yamamori et al. |
| 4,425,346 A | 1/1984 | Horlington et al. |
| 4,474,451 A | 10/1984 | Mizokami |
| 4,478,818 A | 10/1984 | Shell et al. |
| 4,494,274 A | 1/1985 | Thurlow |
| 4,521,210 A | 6/1985 | Wong |
| 4,599,353 A | 7/1986 | Bito |
| 4,649,151 A | 3/1987 | Dougherty et al. |
| 4,656,186 A | 4/1987 | Bommer et al. |
| 4,668,506 A | 5/1987 | Bawa |
| 4,675,338 A | 6/1987 | Bommer et al. |
| 4,693,885 A | 9/1987 | Bommer et al. |
| 4,712,500 A | 12/1987 | Montandon |

(Continued)

FOREIGN PATENT DOCUMENTS

| | | |
|---|---|---|
| CA | 1333770 | 10/1988 |
| CA | 1333770 | 1/1995 |

(Continued)

OTHER PUBLICATIONS

Theng et al., Pharmacokinetic and Toxicity Study of an Intraocular Cyclosporine DDS in the Anterior Segment of Rabbit Eyes, Invest Ophthalmol Vis Sci. Nov. 2003;44(11):4895-9, printed from http://www.ncbi.nlm.nih.gov/pubmed/14578414, Abstract only, 2 pages.*
Amrite et al., Ocular Distribution of Intact Nano- & MicroParticles Following Subconjunctival & Systemic Routes of Administration, Drug Delivery Technology, Issue Date: vol. 3 No. 2 Mar./Apr. 2003, 8 pages.*
Croasdale et al., Subconjunctival Corticosteroid Injections for Nonnecrotizing Anterior Scleritis, Arch Ophthalmol. 1999;117(7):966-968.*
de Rojas Silva et al., Efficacy of subconjunctival cyclosporincontaining microspheres on keratoplasty rejection in the rabbit, Graefes Arch Clin Exp Ophthalmol. Oct. 1999;237(10):840-7, printed from http://www.ncbi.nlm.nih.gov/pubmed/10502059, Abstract only.*

(Continued)

*Primary Examiner* — Gigi Huang
(74) *Attorney, Agent, or Firm* — Laura L. Wine; Debra D. Condino

(57) ABSTRACT

Compositions, and methods of using such compositions, useful for injection into the posterior segments of human or animal eyes are provided. Such compositions include small particles of a poorly soluble therapeutic agent that facilitates formation of concentrated regions of the therapeutic agent in the retinal pigmented epithelium of an eye. The particles are formed by combining a therapeutic agent with an ophthalmically acceptable polymer component. The particles have sizes less than about 3000 nanometers, and in some cases, less than about 200 nanometers. One example of a composition includes particles of triamcinolone acetonide and hyaluronic acid have a size less than about 3000 nanometers.

2 Claims, No Drawings

(56) References Cited

U.S. PATENT DOCUMENTS

| | | |
|---|---|---|
| 4,727,064 A | 2/1988 | Pitha |
| 4,853,224 A | 8/1989 | Wong |
| 4,863,457 A | 9/1989 | Lee |
| 4,865,846 A | 9/1989 | Kaufman |
| 4,866,168 A | 9/1989 | Dougherty et al. |
| 4,920,104 A | 4/1990 | DeVore et al. |
| 4,932,934 A | 6/1990 | Dougherty et al. |
| 4,935,498 A | 6/1990 | Sessler et al. |
| 4,959,217 A | 9/1990 | Sanders et al. |
| 4,968,715 A | 11/1990 | Dougherty et al. |
| 4,981,871 A | 1/1991 | Abelson |
| 4,997,652 A | 3/1991 | Wong |
| 5,002,962 A | 3/1991 | Pandey et al. |
| 5,017,579 A | 5/1991 | Gubin et al. |
| 5,019,400 A | 5/1991 | Gombotz et al. |
| 5,028,621 A | 7/1991 | Dougherty et al. |
| 5,034,413 A | 7/1991 | Chan et al. |
| 5,075,115 A | 12/1991 | Brine |
| 5,077,049 A | 12/1991 | Dunn et al. |
| 5,089,509 A | 2/1992 | Chandraratna |
| 5,093,349 A | 3/1992 | Pandey et al. |
| 5,100,431 A | 3/1992 | Buster et al. |
| 5,106,615 A | 4/1992 | Dikstein |
| 5,164,188 A | 11/1992 | Wong |
| 5,166,331 A | 11/1992 | Della Valle et al. |
| 5,169,638 A | 12/1992 | Dennis et al. |
| 5,171,741 A | 12/1992 | Dougherty |
| 5,173,504 A | 12/1992 | Dougherty |
| 5,190,966 A | 3/1993 | Dougherty et al. |
| 5,198,460 A | 3/1993 | Pandey et al. |
| 5,209,926 A | 5/1993 | Babcock et al. |
| 5,252,319 A * | 10/1993 | Babcock et al. ............ 424/78.04 |
| 5,256,408 A | 10/1993 | Babcock et al. |
| 5,268,178 A | 12/1993 | Calhoun et al. |
| 5,300,114 A | 4/1994 | Gwon et al. |
| 5,314,905 A | 5/1994 | Pandey et al. |
| 5,324,519 A | 6/1994 | Dunn et al. |
| 5,324,718 A | 6/1994 | Loftsson et al. |
| 5,332,582 A | 7/1994 | Babcock et al. |
| 5,356,629 A | 10/1994 | Sander et al. |
| 5,378,475 A | 1/1995 | Smith et al. |
| 5,385,887 A | 1/1995 | Yim et al. |
| 5,438,071 A | 8/1995 | Clauss et al. |
| 5,443,505 A | 8/1995 | Wong et al. |
| 5,459,159 A | 10/1995 | Pandey et al. |
| 5,466,233 A | 11/1995 | Weiner et al. |
| 5,487,897 A | 1/1996 | Polson et al. |
| 5,494,901 A | 2/1996 | Javitt et al. |
| 5,496,811 A * | 3/1996 | Aviv ................. A61K 9/1075 514/546 |
| 5,501,856 A | 3/1996 | Ohtori et al. |
| 5,504,074 A | 4/1996 | D'Amato et al. |
| 5,516,522 A | 5/1996 | Peyman et al. |
| 5,552,160 A | 9/1996 | Liversidge et al. |
| 5,565,188 A | 10/1996 | Wong et al. |
| 5,576,311 A | 11/1996 | Guy et al. |
| 5,587,371 A | 12/1996 | Sessler et al. |
| 5,587,479 A | 12/1996 | Makovec et al. |
| 5,597,897 A | 1/1997 | Ron et al. |
| 5,655,832 A | 8/1997 | Pelka et al. |
| 5,656,297 A | 8/1997 | Bernstein et al. |
| 5,688,819 A | 11/1997 | Woodward et al. |
| 5,702,716 A | 12/1997 | Dunn et al. |
| 5,707,643 A | 1/1998 | Ogura |
| 5,717,030 A | 2/1998 | Dunn et al. |
| 5,744,155 A | 4/1998 | Friedman et al. |
| 5,747,061 A | 5/1998 | Amselem et al. |
| 5,766,242 A | 6/1998 | Wong et al. |
| 5,770,589 A | 6/1998 | Billson et al. |
| 5,776,699 A | 7/1998 | Klein et al. |
| 5,780,044 A | 7/1998 | Yewey et al. |
| 5,798,349 A | 8/1998 | Levy et al. |
| 5,824,072 A | 10/1998 | Wong |
| 5,824,074 A | 10/1998 | Koch |
| 5,869,079 A | 2/1999 | Wong et al. |
| 5,877,207 A | 3/1999 | Klein et al. |
| 5,882,682 A | 3/1999 | Rork et al. |
| 5,886,030 A | 3/1999 | Maniar |
| 5,906,920 A | 5/1999 | Evans et al. |
| 5,913,884 A | 6/1999 | Trauner et al. |
| 5,919,970 A | 7/1999 | Song et al. |
| 5,922,773 A | 7/1999 | Lipton et al. |
| 5,958,954 A | 9/1999 | Klein et al. |
| 6,051,576 A | 4/2000 | Ashton et al. |
| 6,066,675 A | 5/2000 | Wen et al. |
| 6,074,661 A | 6/2000 | Olejnik et al. |
| 6,107,347 A | 8/2000 | Francese et al. |
| 6,143,314 A | 11/2000 | Chandrashekar et al. |
| 6,193,997 B1 | 2/2001 | Modi |
| 6,217,869 B1 | 4/2001 | Meyer et al. |
| 6,217,895 B1 | 4/2001 | Guo et al. |
| 6,225,303 B1 | 5/2001 | Miller et al. |
| 6,258,319 B1 | 7/2001 | Hearst et al. |
| 6,261,583 B1 | 7/2001 | Dunn et al. |
| 6,270,492 B1 | 8/2001 | Sinofsky |
| 6,270,749 B1 | 8/2001 | Blumenkranz et al. |
| 6,271,216 B1 | 8/2001 | Mello et al. |
| 6,271,220 B1 | 8/2001 | Garst et al. |
| 6,274,614 B1 | 8/2001 | Richter et al. |
| 6,290,713 B1 | 9/2001 | Russell |
| 6,294,361 B1 | 9/2001 | Horowitz et al. |
| 6,306,426 B1 | 10/2001 | Olejnik et al. |
| 6,317,616 B1 | 11/2001 | Glossop |
| 6,319,273 B1 | 11/2001 | Chen et al. |
| 6,331,313 B1 | 12/2001 | Wong et al. |
| 6,357,568 B1 | 3/2002 | Chen |
| 6,369,116 B1 | 4/2002 | Wong et al. |
| 6,387,409 B1 | 5/2002 | Khan et al. |
| 6,395,293 B2 | 5/2002 | Polson et al. |
| 6,395,294 B1 | 5/2002 | Peyman |
| 6,403,649 B1 | 6/2002 | Woodward et al. |
| 6,407,079 B1 | 6/2002 | Muller et al. |
| 6,455,062 B1 | 9/2002 | Olejnik et al. |
| 6,461,631 B1 | 10/2002 | Dunn et al. |
| 6,482,854 B1 | 11/2002 | Lipton et al. |
| 6,497,729 B1 | 12/2002 | Moussy et al. |
| 6,537,568 B2 | 3/2003 | Olejnik et al. |
| 6,548,078 B2 | 4/2003 | Guo et al. |
| 6,565,871 B2 | 5/2003 | Roser et al. |
| 6,565,874 B1 | 5/2003 | Dunn et al. |
| 6,573,280 B2 | 6/2003 | Dreyer |
| 6,595,945 B2 | 7/2003 | Brown |
| 6,699,493 B2 | 3/2004 | Wong |
| 6,713,081 B2 | 3/2004 | Robinson et al. |
| 6,713,268 B2 | 3/2004 | Woodward et al. |
| 6,723,353 B2 | 4/2004 | Beck et al. |
| 6,726,918 B1 | 4/2004 | Wong et al. |
| 6,765,012 B2 | 7/2004 | Andrews et al. |
| 6,835,202 B2 | 12/2004 | Harth et al. |
| 6,899,717 B2 | 5/2005 | Weber et al. |
| 7,087,237 B2 | 8/2006 | Peyman |
| 7,125,542 B2 | 10/2006 | Miller |
| 7,354,574 B2 | 4/2008 | Peyman |
| 8,569,272 B2 * | 10/2013 | Lyons et al. ................. 514/169 |
| 2002/0012704 A1 | 1/2002 | Pace et al. |
| 2002/0094998 A1 | 7/2002 | Burke |
| 2002/0198174 A1 | 12/2002 | Lyons |
| 2003/0060763 A1 | 3/2003 | Penfold et al. |
| 2003/0069286 A1 | 4/2003 | Chen |
| 2003/0095995 A1 | 5/2003 | Wong |
| 2003/0108616 A1 | 6/2003 | Bosch et al. |
| 2003/0171320 A1 | 9/2003 | Guyer |
| 2003/0195179 A1 | 10/2003 | Sawa |
| 2003/0211123 A1 | 11/2003 | Shukla et al. |
| 2003/0225152 A1 | 12/2003 | Andrews et al. |
| 2004/0024069 A1 | 2/2004 | Chen et al. |
| 2004/0029771 A1 * | 2/2004 | Rigdon ................. A61K 9/0048 514/1 |
| 2004/0054374 A1 | 3/2004 | Weber et al. |
| 2004/0077562 A1 | 4/2004 | Chandavarkar et al. |
| 2004/0137059 A1 | 7/2004 | Nivaggioli et al. |
| 2004/0152664 A1 | 8/2004 | Chang et al. |
| 2005/0089545 A1 * | 4/2005 | Kuwano et al. ............. 424/427 |
| 2005/0101582 A1 | 5/2005 | Lyons et al. |

(56) References Cited

U.S. PATENT DOCUMENTS

| | | | |
|---|---|---|---|
| 2005/0181017 A1 | 8/2005 | Hughes et al. |
| 2005/0244458 A1 | 11/2005 | Huang et al. |
| 2005/0244461 A1 | 11/2005 | Nivaggioli et al. |
| 2005/0244462 A1 | 11/2005 | Farooq |
| 2005/0244463 A1 | 11/2005 | Huang et al. |
| 2005/0244464 A1 | 11/2005 | Hughes |
| 2005/0244465 A1 | 11/2005 | Nivaggioli et al. |
| 2005/0244466 A1 | 11/2005 | Whitcup et al. |
| 2005/0244468 A1 | 11/2005 | Huang |
| 2005/0244470 A1 | 11/2005 | Hughes et al. |
| 2005/0244471 A1 | 11/2005 | Shiah et al. |
| 2005/0244474 A1 | 11/2005 | Huang et al. |
| 2005/0244478 A1 | 11/2005 | Hughes et al. |
| 2005/0244479 A1 | 11/2005 | Huang |
| 2005/0250737 A1 | 11/2005 | Hughes et al. |
| 2006/0009498 A1 | 1/2006 | Whitcup |
| 2006/0141049 A1 | 6/2006 | Lyons |
| 2006/0205639 A1 | 9/2006 | Domb et al. |
| 2007/0298073 A1 | 12/2007 | Whitcup et al. |
| 2007/0298074 A1 | 12/2007 | Robinson et al. |
| 2008/0299206 A1 | 12/2008 | Lee et al. |

FOREIGN PATENT DOCUMENTS

| | | | |
|---|---|---|---|
| EP | 0 197 718 A2 | 3/1986 |
| EP | 0197718 A2 | 3/1986 |
| EP | 0197718 | 10/1986 |
| EP | 0 244 178 | 4/1987 |
| EP | 0244178 | 11/1987 |
| EP | 0 364 417 | 9/1989 |
| EP | 0364417 | 9/1989 |
| EP | 0 430 539 | 6/1991 |
| EP | 0 488 401 | 6/1992 |
| EP | 0488401 | 6/1992 |
| EP | 0430539 | 10/1994 |
| GB | 2211848 A | 7/1989 |
| JP | 2000-247871 | 9/2000 |
| WO | 8901772 | 3/1989 |
| WO | 9119482 | 12/1991 |
| WO | 9300076 A1 | 1/1993 |
| WO | WO 9300076 A1 | 1/1993 |
| WO | 9513765 | 5/1995 |
| WO | WO 95/13765 | 5/1995 |
| WO | 9638174 | 12/1996 |
| WO | WO 96/38174 | 12/1996 |
| WO | 0002564 | 1/2000 |
| WO | WO 00/02564 | 1/2000 |
| WO | 0130323 | 5/2001 |
| WO | WO 01/30323 | 5/2001 |
| WO | 0158240 | 8/2001 |
| WO | WO 01/58240 | 8/2001 |
| WO | 02-05815 | 1/2002 |
| WO | 0202076 | 1/2002 |
| WO | WO 02/02076 | 1/2002 |
| WO | WO 02/05815 | 1/2002 |
| WO | 0243785 | 6/2002 |
| WO | WO 02/43785 | 6/2002 |
| WO | 02089815 | 11/2002 |
| WO | WO 02/089815 | 11/2002 |
| WO | 02100437 | 12/2002 |
| WO | WO 02/100437 | 12/2002 |
| WO | WO 03070219 A1 * | 8/2003 |
| WO | WO03-089008 | 10/2003 |
| WO | 2004069280 | 8/2004 |
| WO | WO 2004/069280 | 8/2004 |
| WO | 2004087043 | 10/2004 |
| WO | WO 2004/087043 | 10/2004 |
| WO | 2005072701 A1 | 8/2005 |
| WO | 2005110380 A1 | 11/2005 |
| WO | WO 2005/110380 | 11/2005 |

OTHER PUBLICATIONS

ALPHAGAN® P, Product Information, Allergan, Inc. 2005, Irvine, CA.

Anderson, L.C. et al., *An Injectable Substained Release Fertility Control System*, Contraception, 1976;, 13:375-384.

Antcliff R., et al Marshal J., *The pathogenesis of edema in diabetic maculopathy*, Seminars in Oththalmology, 1999; 14:223-232.

Arrnaly M., *Statistical attributes of the steroid hypertensive response in the clinically normal eye*, Investigative Ophthalmology and Visual Science, 1965; 4:187-197.

Audren, F. et al., *Pharmacokinetic-Pharmacodynamic modeling of the effect of Triamcinolone Acetonide on Central Macular Thickness in Patients with Diabetic Macular Edema*, Investigative Ophthalmology and Visual Science, 45(10); 3435-3441: Oct. 2004.

Baker R., *Controlled Release of Biologically Active Agents*, A Wiley-Interscience Publication, 1987; 73-75.

Becker B., *Intraocular pressure response to topical corticosteroid*, Investigative Ophthalmology and Visual Science, 1965; 4:198-205.

Bito, L.Z., *Biological protection with prostaglandins*, Cohen, M.M., ed., Boca Raton, Fla., CRC Press Inc., 1985; 31-252.

Bito L.Z., *Glaucom: Applied Pharmacology in the Medical Treatment*, Drance, S.M. and Neufled, A.H. Eds., New York, Grune & Stratton, 1984; 477-505.

Bito L.Z., *Prostaglandins: Old Concepts and New Perspectives*, Archives of Ophthalmology, 1987; 105:1036-1039.

Bodor, N. et al., *A Comparison of Intraocular Pressure Elevating Activity of Loteprednol Etabonate and Dexamethasone in Rabbits*, Current Eye Research, 1992; 11:525-530.

Brubaker, *Mechanism of Action of Bimatoprost (Lumigan™)*, Survey of Ophthalmology, 2001; 45(Suppl 4):S347-S351.

Busse et al., *Tyrosine kinase inhibitors: rationale, mechanisms of action, and implications for drug resistance*, Seminars in Oncology, 2001; 28(suppl 16):47-55.

Butcher J. et al., *Bilateral cataracts and glaucoma induced by long term use of steroid eye drops* British Medical Journal, 1994; 309-343.

Challa, J.K. et al., *Exudative Macular Degenertion and Intravitreal Triamcinolone: 18month follow up*, Australian and New Zealand Journal of Opthalmology 1998; 26:277-281.

Chang et al., *Development of a Topical Suspension Containing Three Active Ingredients*, Drug Development and Industrial Pharmacy, 2002; 28(1):29-39.

Charles J. et al., *Use of Bioerodible Polymers Impregnated with Mitomycin in Glaucoma Filtration Surgery in Rabbits*, Ophthalmology, Apr. 1991; 98(4): 503-508.

Chen et al., *Lumigan®: A Novel Drug for Glaucoma Therapy*, Optometry in Practice 2002; 3:95-102.

Cheng, Cheng-Kuo et al., *Intravitreal Sustained-Release Dexamethasone Device in the Treatment of Experimental Uveitis*, Investigative Ophthalmolgy & Visual Science, Feb. 1995; 36(2):442-453.

Chiang et al., *Pharmacokinetics and Intraocular Pressure Lowering Effect of Timolol Preparation in Rabbit Eyes*, Journal of Ocular Pharmacology and Therapeutics, 1996; 12(4):471-480.

Coleman et al., *A 3-Month Randomized Controlled Trial of Bimatoprost (LUMIGAN) Versus Combined Timolol and Dorzolamide (Cosopt) in Patients with Glaucoma or Ocular Hypertension*, Ophthalmology, 2003; 110(12):2362-2368.

Company News on Call, "Oculex Announces Positive Clinical Results for Posurdex(R)—The First Biodegradable Ocular Implant in Clinical Trial" Copyright © 1996-2004 PR Newswire Association LLC.

Coquelet et al., *Successful Photodynamic Therapy Combined with Laser Photocoagulation in Three Eyes with Classic Subfoveal Choroidal Neovascularization Affecting Two Patients with Mulifocal Choroiditis: Case Reports*, Bulletin of the Society of Belgian Ophthalmologists, 2002; 283:69-73.

Crabb et al., *Cloning of the cDNAs encoding the cellular retinaldehyde-binding protein from bovine and human retina and comparison of the protein structures*, Journal of Biological Chemistry, 1988; 263(35):18688-18692.

Danis R. et al., *Intravitreal triamcinolone acetonide in exudative age-related macular degeneration*, Retina, 2000; 20:244-250.

Dea I. et al., *Hyaluronic acid: a novel, double helical molecule*, Science, Feb. 9, 1973; 179(73):560-562.

(56) References Cited

OTHER PUBLICATIONS

Di Colo G., *Controlled Drug Release From Implantable Matrices Based on Hydrophobic Polymers*, Biomaterials, 1992; 13(12):850-856.
Dunn et al., *ARPE-19, a human retinal pigment epithelial cell line with differentiated properties*, Experimental Eye Research, 1996; 62:155-169.
Edelman et al., *Corticosteroids inhibit VEGF-induced vascular leakage in a rabbit model of blood-retinal and blood-aqueous barrier breakdown*, Experimental Eye Research, Feb. 2005; 80(2):249-258.
Einmahl et al., *Evaluation of a novel biomaterial in the suprachoroidal space of the rabbit eye*, Investigative Ophthalmology & Visual Science, May 2002; 43(5):1533-1539.
Einmahl et al., *Therapeutic applications of viscous and injectable poly (ortho esters)*, Advanced Drug Investigative Ophthalmology and Visual Science, May 2002; 43(5):1533-1539.
*Encyclopedia of Polymer Science and Technology*, vol. 3, Interscience Publishers, Inc., New York, latest edition, Title page TOG Cellular Materials to composites only.
Enyedi, Laura et al., *An Intravitreal Device Providing Sustained Release of Cyclosporine and Dexamethasone*, Current Eye Research, 1995; 549-557.
Epstein, David L., *Primary Open-Angle Glaucoma*, Chandler and Grant's Glaucoma, Lea & Febiger, 1986; 129-181.
Fabbro et al., *Protein tyrosine kinase inhibitors: new treament modalities?*, Current Opinion in Pharmacology, 2002; 2:374-381.
Fotsis et al., *The endogenous oestrogen metabolite 2-methoxyoestradiol inhibits angiogenesis and suppresses tumor growth*, Nature, 1994; 368:237.
Goel et al., *Tyrosine Kinase Inhibitors: A Clinical Perspective*, Current Oncology Reports, 2002; 4:9-19.
Guenther, Lyn C., *Optimizing Treatment with Topical Tazarotene*, American Journal of Clinical Dermatology, 2003; 4(3):197-202.
Hainsworth, Dean P. et al., *Sustained Release Intravitreal Dexamethasone*, Journal of Ocular Pharmacology and Therapeutics, 1996; 12(1):57-63.
Haluska et al., *Receptor tyrosine kinase inhibitors*, Current Opinion in Investigational Drugs, 2001; 2(2):280-286.
Hamel et al., *Molecular cloning and expression of RPE65, a novel retinal pigment epithelium-specific microsomal protein that is post-transcriptionally regulated in vitro*, Journal of Biological Chemistry, 1993; 268(21):15751-15757.
Hare et al., *Efficacy and safety of memantine, an NMDA-Type Open-Channel Blocker, for reduction of retinal injury associated with experimental glaucoma in rat and monkey*, Survey of Ophthalmology, 2001; 45(Suppl 3):S284-S289.
Hashizoe, Mototane et al., *Scleral Plug of Biodegradable Polymers for Controlled Drug Release in the Vitreous*, Archives of Opthalmology, 1994; 112:1380-1384.
Heller J., *Biodegradable Polymers in Controlled Drug Delivery*, CRC Critical Reviews in Therapeutic Drug Carrier Systems, 1987; 1(1):39-90.
Heller J., *Hydrogels in Medicine and Pharmacy*, N.A. Peppes ed., CRC Press, Boca Raton, FL, 1987; 3:137-149.
Helliwell P., *Use of an objective measure of articular stiffness to record changes in finger joints after intra-articular injection of corticosteroid*, Annals of Rheumatic Diseases, 1997; 56:71-73.
Hoyng et al., *Pharmacological Therapy for Glaucoma*, Drugs, Mar. 2000; 59(3):411-434.
Hubbard et al., *Protein tyrosine kinase structure and function*, Annual Review of Biochemistry, 2000: 69:373-398.
Inoue, M. et al., *Vitreous Concentrations of Triamcinolone Acetonide in Human Eyes After Intravitreal or Subtenon Injection*, American Journal of Ophthalmology, 2004; 138(6):1046-8.
Jackanicz et al., *Polyactic Acid as a biodegradable carrier for contraceptive steroids*, Contraception, 1973; 8(3):227-235.
Jampel H. et al, *Glaucoma Filtration Surgery in Monkeys Using 5-Fluorouridine in Polyanhydride Disks*, Archives of Ophthalmology, Mar. 1990; 108:430-435.

Jonas J. et al., *Intravitreal injection of crystalline cortisone as adjunctive treatment of diabetic macular edema*, American Journal of Ophthalmology, 2001; 132:425-427.
Jonas J. et al., *Intravitreal injection of crystalline cortisone as adjunctive treatment of proliferative vitreoretinopathy*, British Journal of Ophthalmology, 2000; 84:1064-1067.
Jonas J. et al., *Intravitreal injection of triamcinolone for diffuse diabetic macular edema*, Archives of Ophthalmology, 2003; 121:57-61.
Kimura, Hideya et al., *A new Vitreal Drug Delivery System using Implantable Biodegradable Polymeric Device*, Investigative Ophthalmology & Visual Science, 1994; 35:2815-2819.
Klimanskaya et al., *Derivation and comparative assessment of retinal pigment epithelium from human embryonic stem cells using transcriptomics*, Cloning and Stem Cells, 2004; 6(3):217-245.
Kochinke, F. et al., *Biodegradable Drug Delivery System for Uveitis Treatment*, Investigative Ophthalmology & Visual Science. Feb. 1996; 37(3):186-B98.
Kwak, H.W. and D'Amico, D.J., *Evaluation of the Retinal Toxicity and Pharmacokinetics of Dexomethasone After Intravitreal Injection*, Archives of Ophthalmology, 1992; 110:259-266.
Lai et al., *Alpha-2 adrenoceptor agonist protects retinal function after acute retinal ischemic injury in the rat*, Visual Neuroscience, 2002; 19:175-185.
Lee D. et al., *Glaucoma Filtration Surgery in Rabbits Using Bioerodible Polymers and 5-Fluorouracil*, Ophthalmology, Dec. 1987; 94(12):1523-1530.
Lee D. et al, *The Use of Bioerodible Polymers and 5-Fluorouracil in Glaucoma Filtration Surgery*, Investigative Ophthalmology & Visual Science, Nov. 1988; 29(11):1692-1697.
"Lumigan®: a new ocular hypotensive agent for achiving target intraocular pressures," Acta Ophthalmologica Scandinavica, Scientific Abstracts, 2002; 80(4):457.
"Lumigan found effective in early phase 3", Ocular Surgery News, Mar. 2001; 19(5):1,35.
Marks R., *Topical Tazarotene: Review and Re-Evaluation*, Retinoids, 2001, 17(3):72-74.
Martidis A. et al., *Intravitreal triamcinolone for refractory diabetic macular edema*, Ophthalmology, 2002; 109:920-927.
Maurice, D.M., *Micropharmaceutics of the Eye*, Ocular Inflammation Therapy, 1983; 1:97-102.
McCarty D. et al., *Inflammatory reaction after intrasynovial injection of microcrystalline adrenocorticosteroid esters*, Arthritis and Rheumatism, 1964; 7(4):359-367.
McCuen B. et al., *The lack of toxicity of intravitreally administered triamcinolone acetonide*, American Journal of Ophthalmology, 1981; 91:785-788.
McGhee et al., *Locally Administered Ocular Corticosteroids Benefits and Risks*; Drug Safety, 2002; 25(1):33-55.
Miller et al., *Degradation rates of oral resorbable implants (polyactates and polyglycolates) rate modification with changes in PLA/PGA copolymer ratios*, Journal of Biomedical Materials Research, 1977; 11:711-719.
Miller et al., *Synthesis and structure-activity profiles of A-Homoestranes, the Estratopones*, Journal of Medical Chemistry, 1997; 40:3836-3841.
Morita Y., et al., *Intravitreous delivery of dexamethasone sodium m-sulfobenzoate from poly (DL-lactic acid) implants*, Biological and Pharmaccutical Bulletin, Feb. 1998; 21(2): 188-90.
Nauck, M., et al., *Corticosteroids inhibit the expression of the vascular endothelial growth factor gene in human vascular smooth muscle cells*, European Journal of Pharmacology, 1998; 341:309-315.
Nauck, M., et al., *Induction of vascular endothelial growth factor by platelet-activating factor and platelet-derived growth factor is downregulated by corticosteroids*, American Journal of Respiratory Cell and Molecular Biology, 1997 ; 16 :398-406.
Nishimura et al., *Isolating Triamcinolone Acetonide Particles for Intravitreal Use with a Porous Membrane Filter*, Retina, The Journal of Retinal and Vitreous Diseases, 2003; 23(6):777-779.

(56) References Cited

OTHER PUBLICATIONS

Olsen, T.W. et al., *Human Scleral Permeability: Effects of Age, Cryotherapy, Transscleral Diode Laser, and Surgical Thinning*, Investigative Ophthalmology & Visual Science, 1995; 36(9):1893-1903.
Pe'er J. et al., *Vascular endothelial growth factor by platelet-activating factor and platelet-derived growth factor upregulation in human central retinal vein occlusion*, Ophthalmology, 1998; 105:412-416.
Penfold P. et al., *Exudative macular degeneration and intravitreal triamcinolone: A pilot study*, Australian and New Zealand Journal of Ophthalmology, 1995; 23:293-298.
Phillips et al., *Efficacy of 0.1% Tazarotene cream for the treatment of photodamage*, Archives of Dermatology, Nov. 2002; 138(11):1486-1493.
Phillips et al., *Penetration of timolol eye drops into human aqueous humour: the first hour*, British Journal of Ophthalmology, 1985; 69:217-218.
Physician's Desk Reference, product information on "Alphagan® P", 54 Edition, 2000; 492-493.
Physician's Desk Reference for Ophthalmic Medicines, 30 Edition, 2002; 285.
Pribluda et al., *2-Methoxyestradiol: an endogenous antiangiogenic and antiproliferative drug candidate*, Cancer and Metastasis Reviews, 2000; 19:173-179.
Quigley et al., *The mechanism of optic nerve damage in experimental acute intraocular pressure elevation*, Investigative Ophthalmology & Visual Science, 1980; 19:505.
Rao et al., *Preparation and Evaluation of Ocular Inserts Containing Norfloxacin*, Turkish Journal of Medical Science, 2004; 34:239-246.
Rao, N.A. et al., *Introcular Inflammation and Uveitis*, In Basic and Clinical Science Course, San Francisco: American Academy of Ophthalmology, 1997-1998; secton 9, 57-80, 102-103, 152-156.
Rechtman et al., *Intravitreal triaminolone with photodynamic therapy for subfoveal choroidal neovascularisation in age related macular degeneration*, British Jounal of Ophthalmology, 2004; 88:344-347.
Renfro, L., et al., *Ocular Effects of Topical and Systemic Steroids*, Dermalologic Clinics, 1992; 10:505-512.
Roff, W.J. and Scott, J.R., Handbook of Common Polymers. CRC Press, Cleveland, OH, latest edition.
Rogojina et al., *Comparing the use of Affymetrix to spotted oligonucleotide microarrays using two retinal pigment epithelium cell lines*, Molecular Vision, 2003; 9:482-496.
Roth D. et al., *Noninfectious endophthalmitis associated with intravitreal triamcinolone injection*, Archives of Ophthalmology, 2003; 121:1279-1282.
Schindler, R.H. et al., *The Clearance of Intravitreal Triamcinolone Acetonide*, American Journal of Opthalmology, 1982; 93: 415-417.
Scholes, G.N. et al., *Clearance of Triamcinolone From Vitreous*, Archives of Ophthalmololgy, 1985; 103:1567-1569.
Schuettauf et al., *Effects of anti-glaucoma medications on ganglion cell survival: the DBA/2J mouse model*, Vision Research, 2002; 42(20):2333-2337.
Schumacher et al., *The physiological estrogen metabolite 2-methoxyestradiol reduced tumor growth and induces apoptosis in human solid tumors*, Journal of Cancer Research and Clinical Oncology, 2001; 127:405-410.
Schwartz, B., *The Response of Ocular Pressure to Corticosteroids*, Ophthalmology Clinics of North America; 1966; 6:929-989.
Siebold et al., Prodrug 5, 3 (1989).
Skalka, H.W. et al., *Effect of Corticosteroids on Cataract Formation*, Archives of Ophthalmology, 1980; 98:1773-1777.
Smith et al., *Sustained-release subconjunctival 5-fluorouracil*, Ophthalmic Surgery and Laser, Sep. 1996; 27(9):763-767.
Starr, M.S., *Further Studies on the Effect of Prostaglandin on Intraocular Pressure in the Rabbit*, Experimental Eye Research, 1971; 11:170-177.

Streilein et al., *Ocular immune privilege; therapeutic opportunities from an experiment of nature*, Nature Review Immunology, 2003; 3:879-889.
Survey of Ophthalmology 2002; 47(3); 295.
Sutter F. et al., *Pseudo-endophthalmitis after intravitreal injection of triamcinolone*, British Journal of Ophthalmology, 2003; 87;972-974.
Tan, D.T.H. et al., *Randomized Clinical Trial of a New Dexamethasone Delivery System (Surodex) for Treating of Post-Cataract Surgery Inflammation*, Ophthalmology, 1999; 106(2):223-231.
"Tazarotene", Drugs Future, 2003; 28(2):208-209. Annual Update 2003: Dermatologic Drugs.
TAZORAC®, Allergan, Product Information.
Tracy et al., *Factors affecting the degradation rate of poly (lactide-co-glycolide) Microspheres in vivo and in vitro*, Biomaterials, 1999; 20:1057-1062.
United States Pharmacopeia, The National Formulary, USP 23/NF 18; 1195; pp. 1790-1798.
Watson et al., *A Six-month, Randomized, Double-masked Study Comparing Latanoprost with Timolol in Open-angle Glaucoma and Ocular Hypertension*, Ophthalmology, 1996; 103:126-137.
Wheeler, *Experimental studies of agents with potential neuroprotective properties*, Acta Ophthalmologica Scandinavica, 1999; 77(229):27-28.
Wheeler et al, *Role of Alpha-2 Agonists in Neuroprotection*, Survey of Ophthalmology, Apr. 2003; 48(Suppl 1):S47-S51.
WoldeMussie, *Neuroprotection of retinal ganglion cells in experimental models of glaucoma*, Minerva Oftalmol, 2000; 42(2):71-78.
WoldeMussie et al., *Neuroprotective effects of memantine in different retinal injury in rats*, Journal of Glaucoma, 2002; 11(6):474-480.
Woodward et al., *AGN 2024 (Lumigan®): A Synthetic Prostamide Analog that Lowers Primate Intraocular Pressure by Virtue of Its Inherent Pharmacological Activity*, ARVO 2002; (CD-ROM):POS.
Woodward et al., "The Pharmacology of Bimatoprost (Lumigan™)", Survey of Ophthalmology, 2001; 45(Suppl 4):S337-S345.
Yeung et al., *Cytotoxicity of Triamcinolone on Cultured Human Retinal Pigment Epithelial Cells: Comparison with Dexamethasone and Hydrocortisone*, Japanese Journal of Ophthalmology, 2004; 48:236-242.
Zhou, T. et al., *Development of a Multiple-Drug Delivery Implant for Introcular Mangement of Proliferative Vitreoretinopathy*, Journal of Controlled Release, 1998; 55:281-295.
The Merck Index. Hydrocortisone, 2009, 14th Edition, printed from Http://www.knovel.com/web/portal/knovel_content?p..p_id=EXT..KNOVEL_C...KNOVEL_CONTENT_subSubjectAreaID=0&_EXT_KNOVEL..IsSearch=true printed May 19, 2010, 3 pages.
Aukunuru et al., "In Vitro Delivery of Nano- and Micro-Particles to Human Retinal Pigment Epithelial (ARPE-19) Cells," Drug Delivery Technologies, 2002;2(2):50-57.
Beer et al., "Intraocular Concentration and Pharmacokinetics of Triamcinolone Acetonide after a Single Intravitreal Injection," Ophthalmology, vol. 110, No. 4, pp. 681-686, Apr. 2003.
Kompella et al., "Subconjuctival Nano- and Microparticles Sustain Retinal Delivery of Budesondie, a Corticosteroid Capable of Inhibiting VEGF Expression," Investigatvie Ophthalmology & Visual Science, Mar. 2003, vol. 44, No. 3, pp. 1192-1201.
Aldrich, Fabrication—Syringe Needle Dimensions, 1994-1995 Catalog/Handbook of Fine Chemicals, printed from http://academic.evergreen.edu/projects/biophysics/technotes/fabric/syringe.htm, 2 pages.
Jonas, Concentration of intravitrcal injected triamcinolone acetonide in aqueous humore, Br. J. Ophthalmol 2002;86:1066, printed from http://bio.bmj.com/content/86/9/1066.1.full.html, 2 pages.
International Search Report—PCT/US2012/064985 received Feb. 21, 2013.
International Search Report—PCT/US2012/064998, received Jan. 24, 2013.

(56) References Cited

OTHER PUBLICATIONS

International Search Report—PCT/US2012/064988, received Jan. 23, 2013.
International Search Report—PCT/US2012/065011, received Jan. 25, 2013.
U.S. Appl. No. 60/567,339, filed Apr. 30, 2004.
U.S. Appl. No. 60/567,423, filed Apr. 20, 2004.
U.S. Appl. No. 60/587,032, filed Jul. 12, 2004.
Aldrich, Fabrication-Syringe Needle Dimensions, Catalog/Handbook of Fine Chemicals, 1994-1995, http://academic.evergreen.edu/projects/biophysics/technotes/fabric/syringe.htm; 2 pages.
Allergan, Alphagan Product Information, Product Sheet, 2005, 1-10.
Anderson, Lynne et al., An Injectable Sustained Release Fertility Control System, Contraception, 1976, 375-384, 13.
Antcliff, R.J. et al., The Pathogenesis of Edema in Diabetic Maculopathy, Seminars in Ophthalmology, Dec. 1999, 223-232, 14(4).
Armaly, Mansour, Statistical Attributes of the Steroid Hypertensive Response in the Clinically Normal Eye, Investigative Ophthalmology, Apr. 1965, 187-197, 4(2).
Audren, Francois et al., Pharmacokinetic-Pharmacodynamic Modeling of the Effect of Triamcinolone Acetonide on Central Macular Thickness in Patients with Diabetic Macular Edema, Invest. Ophthalmol. Vis. Sci., 2004, 3435-3441, 45.
Aukunuru, Jithan et al., In Vitro Delivery of Nano- and Micro-Particles to Human Retinal Pigment Epithelial (ARPE-19) Cells, Drug Delivery Technologies, 2002, 50-57, 2(2).
Baker, Richard W., Controlled Release of Biologically Active Agents, John Wiley & Sons, New York, 1987, 73-75.
Becker, Bernard, Intraocular Pressure Response to Topical Corticosteroids, Investigative Ophthalmology, Apr. 1965, 198-205, 4 (2).
Beer, Paul et al., Intraocular Concentration and Pharmacokinetics of Triamcinolone Acetonide After a Single Intravitreal Injection, Opthalmology, Apr. 2003, 681-686, 110(4), US.
Bito, LZ, Biological Protection with Prostanoids, CRC Press, Inc., 1985, 231-252, 1, Cohen, M. M., ed., Boca Raton, FL.
Bito, LZ, Prostaglandins, Old Concepts and New Perspectives, Archives of Ophthalmology, 1987, 1036-1039, 105.
Bito, LZ, Prostaglandins, Other Eicosanoids, and Their Derivatives as Potential Antiglaucoma Agents, Glaucoma: Applied Pharmacology, 1984, 477-505, 20.
Bodor, Nicholas et al., A Comparison of Intraocular Pressure Elevating Activity of Loteprednoletabonate and Dexamethasone in Rabbits, Current Eye Research, 1992, 525-530, 11.
Bowen, P., Particle Size Distribution Measurement From Millimeters to Nanometers and From Rods to Platelets, Journal of Dispersion Science and Technology, 2002, 631-662, 23(5).
Brubaker, Richard, Mechanism of Action of Bimatoprost (LumiganTM), Sury Ophthalmol, 2001, S347-S351, 45- Suppl 4.
Busse, Dagmar et al., Tyrosine Kinase Inhibitors: Rationale, Mechanisms of Action, and Implications for Drug Resistance, Semin Oncol, 2001, 47-55, 28-Suppl 16.
Butcher, Jeremy et al., Bilateral Cataracts and Glaucoma Induced by Long Term Use of Steroid Eye Drops, Bristish Medical Journal, Jul. 2, 1994, 43, 309.
Challa, Jagannadh et al., Exudative Macular Degeneration and Intravitreal Triamcinolone: 18 Month Follow Up, Australian and New Zealand Journal of Ophthalmology, 1998, 277-281, 26.
Chang, H.C. et al., Development of a Topical Suspension Containing Three Active Ingredients, Drug Development and Industrial Pharmacy, 2002, 29-39, 28(1).
Charles, Jean-Bernard et al., Use of Bioerodible Polymers Impregnated with Mitomycin in Glaucoma Filtration Surgery in Rabbits, Ophthalmology, Apr. 1991, 503-508, 98-4.
Chen, June et al., LumiganR: A Novel Drug for Glaucoma Therapy, Optom in Pract., Jun. 12, 2002, 95-102, 3.
Cheng, Cheng-Kuo et al., Intravitreal Sustained-Release Dexamethasone Device in the Treatment of Experimental Uveites, Investigative Ophthalmology and Visual Science, 1995, 442-453, 96 (2), US.
Chiang, Chiao-Hsi et al., Pharmacokinetics and Intraocular Pressure Lowering Effect of Timolol Preparations in Rabbit Eyes, Journal of Ocular Pharmacology and Therapeutics, 1996, 471-480, 12(4).
Coleman, Anne et al., A 3-Month Randomized Controlled Trial of Bimatoprost (Lumigan) Versus Combined Timolol and Dorzolamide (Cosopt) in Patients with Glaucoma or Ocular Hypertension, Ophthalmology, 2003, 2362-8, 110-12.
Coquelet, P. et al., Successful Photodynamic Therapy Combined with Laser Photocoagulatio in Three Eyes With Classic Subfoveal Choroidal Neovascularisation Affecting Two Patients With Multifocal Choroiditis: Case Reports, Bull. Soc. Belge Ophthalmal, 2002, 69-73, 283.
Crabb, John W. et al., Cloning of the cDNAs Encoding the Cellular Retinaldehyde-binding Protein from Bovine and Human Retina and Comparison of the Protein Structures, American Society for Biochemistry and Molecular Biology, Dec. 1988, 18688-18692, vol. 263, No. 35, US.
Danis, Ronald P., et al., Intravitreal Triamconolone Acetonide in Exudative Age-Related Macular Degeneration Lippincott Williams and Wilkins, 2000, 9 pages, vol. 20, No. 3.
DEA, ICM, et al., Hyaluronic Acid: A Novel, Double Helical Molecule, Science, 1973, pp. 560-562, 179.
Di Colo, Giacomo, Controlled Drug Release From Implantable Matrices Based on Hydrophobic Polymers, Biomaterials, 1992, 850-856, 13(12).
Dunn, K.C., ARPE-19, A Human Retinal Pigment Epithelial Cell Line with Differentiated Properties, Experimental Eye Research, 1996, 155-169, 62, Academic Press Limited.
Edelman, Jeffrey et al., Corticosteroids Inhibit VEGF-Induced Vascular Leakage in a Rabbit Model of Blood-Retinal and Blood-Aqueous Barrier Breakdown, Experimental Eye Research, 2005, 249-258, 80.
Einmahl, Suzanne et al., Evaluation of a Novel Biomaterial in the Suprachoroidal Space of the Rabbit Eye, Investigative Opthalmology and Visual Science, May 2002, 1533-1539, 43 (5).
Einmahl, Suzanne et al., Therapeutic applications of viscous and injectable Poly(ortho Esters), Advanced Drug Delivery Reviews, 2001, 45-73, 53.
Encyclopedia of Polymer Science and Technology, John Wiley, 2003, vol. 3, Interscience Publishers, Inc.
Enyedi, Laura et al., An Intravitreal Device Providing Sustained Release of Cyclosporine and Dexamethasone, Current Eye Research, 1996, 549-557, 15(5).
Epstein, David L., Primary Open-Angle Glaucoma, Chandler and Grant's Glaucoma, 1986, 129-181, Lea and Febiger.
Fabbro, Doriano et al., Protein Tyrosine Kinase Inhibitors: New Treatment Modalities?, Current Opinion in Pharmacology, 2002, 374-381, 2.
Fotsis, Theodore et al., The Endogenous Oestrogen Metabolite 2-Methoxyoestradiol Inhibits Angiogenesis and Suppresses Tumour Growth, Letters to Nature, Mar. 17, 1994, 237-239, 368.
Goel, Sanjay et al., Tyrosine Kinase Inhibitors: A Clinical Perspective, Current Oncology Reports, 2002, 9-19, 4.
Goodman and Gilman, Goodman and Gilman's: The Pharmacological Basis of Therapeutics, 1980, 8th Edition, Pergamon Press; New York.
Guenther, Lyn C., Optimizing Treatment with Topical Tazarotene, American Journal of Clinical Dermatology, 2003, 197-202, 4(3).
Hainsworth, Dean P. et al., Sustained Release Intravitreal Dexamethasone, Journal of Ocular Pharmacology and Therapeutics, 1996, 57-63, 12(1).
Haluska, P., et al., Receptor tyrosine kinase inhibitors, Current Opinion in Investigational Drugs, 2001, 280-286, vol. 2, No. 2.
Hamel, Christian P. et al., Molecular Cloning and Expression of RPE65, a Novel Retinal Pigment Epithelium-Specific Microsomal Protein That is Post-Transcriptionally Regulated in Vitro, 1993, 15751-15757, 268(21).
Hare, William et al, Efficacy and Safety of Memantine, an NMDA-Type Open-Channel Blocker, for Reduction of Retinal Injury Asso-

(56) References Cited

OTHER PUBLICATIONS ciated With Experimental Glaucoma in Rat and Monkey, Survey of Opthalmology, 2001, S2843289, 45(Suppl 3).
Hashizoe, Mototane et al., Scleral Plug of Biodegradable Polymers for Controlled Drug Release in the Vitreous, Archives of Ophthalmology, 1994, 1380-1384, 112.
Heller, J., Hydrogels in Medicine and Pharmacy, N.A. Peppes ed., 1987, 137-149, 3, CRC Press, Boca Raton, FL.
Heller, Jorge, Biodegradable Polymers in Controlled Drug Delivery, CRC Critical Reviews in Therapeutic Drug Carrier Systems, 1987, 39-90, 1(1).
Helliwell, Philip, Use of an objective measure of articular stiffness to record changes in finger joints after intra-articular injection of corticosteroid, Annals of Rheumatic Diseases, 1997, 71-73, 56.
Hoyng, Philip et al., Pharmacological Therapy for Glaucoma, Drugs, 2000, 411-434, 59(3), US.
Hubbard, Stevan et al., Protein Tyrosine Kinase Structure and Function, Annual Review of Biochemistry, 2000, 373-398, 69.
Inoue, Makoto et al., Vitreous Concentrations of Triamcinolone Acetonide in Human Eyes After Intravitreal or Subtenon Injection, American Journal of Ophthalmology, 2004, 1046-1048, 138(6).
International Search Report, PCT/US2012/064985, received Feb. 21, 2013.
International Search Report, PCT/US2012/064988, Received Jan. 23, 2013.
International Search Report, PCT/US2012/064998, Received Jan. 24, 2013.
International Search Report, PCT/US2012/065011, Received Jan. 25, 2013.
Jackanicz, Theodore et al., Polyactic Acid as a Biodegradable Carrier for Contraceptive Steroids, Contraception, 1973, 227-235, 8(3).
Jampel, Henry et al., Glaucoma Filtration Surgery in Monkeys Using 5-Fluorouridine in Polyanhydride Disks, Archives of Opthalmology, Mar. 1990, 430-435, 108.
Jonas J. et al., Intravitreal Injection of Triamcinolone for Diffuse Diabetic Macular Edema, Archives of Opthalmology, 2003, 57-61, 121.
Jonas, Jost B., Concentration of intravitreally injected triamcinolone acetonide in aqueous humour, British Journal of Ophthalmology, 2002, 1066-1069, 86, group.bmj.com.
Jonas, Jost B., et al., Intraocular Injection of Crystalline Cortisone as Adjunctive Treatment of Diabetic Macular Edema, American Journal of Ophthalmology, Sep. 2001, 425-427, vol. 132, No. 3.
Jonas, Jost et al, Intravitreal Injection of Crystalline Cortisone as Adjunctive Treatment of Proliferative Vitreoretinopathy, British Journal of Ophthalmology, 2000, 1064-1067, 84.
Kimura, Hideya et al., A New Vitreal Drug Delivery System Using an Implantable Biodegradable Polymeric Device, Investigative Ophthalmology and Visual Science, 1994, 2815-2819, 35.
Klimanskaya, Irina et al., Derivation and Comparative Assessment of Retinal Pigment Epithelium From Human Embryonic Stem Cells Using Transcriptomics, Cloning and Stem Cells, 2004, 217-245, 6(3).
Kochinke, F. et al., Biodegradable Drug Delivery System for Uveitis Treatment, Investigative Ophthalmology & Visual Science, Feb. 1996, 186-B98, 37(3).
Kompella, Uday et al., Subconjunctival Nano-And Microparticles Sustain Retinal Delivery of Budesonide, A Corticosteroid Capable of Inhibiting VEGF Expression, Investigative Ophthalmology and Visual Science, 2003, 1192-1201, 44(3), US.
Kwak, Hyung Woo et al., Evaluation of the Retinal Toxicity and Pharmacokinetics of Dexamethasone After Intravitreal Injection, Archives of Ophthalmology, 1992, 259-266, 110.
Lai, Ronald et al., Alpha-2 Adrenoceptor Agonist Protects Retinal Function After Acute Retinal Ischemic Injury in the Rat, Visual Neuroscience, 2002, 175-185, 19.
Lee, David et al., Glaucoma Filtration Surgery in Rabbits Using Bioerodible Polymers and 5-Fluorouacil, Ophthalmology, Dec. 1987, 1523-1530, 94(12).

Lee, David et al., The Use of Bioerodible Polymers and 5-Fluorouracil in Glaucoma Filtration Surgery, Investigative Ophthalmology and Visual Science, Nov. 1988, 1692-1697, 29(11).
Lumigan: a new ocular hypotensive agent for achieving target intraocular pressures, Acta Ophthalmologica Scandinavica, 2002, 457, 80(4), Scientific Abstracts.
Marks, R., Topical Tazarotene: Review and Re-Evaluation, Retinoids, 2001, 72-74, 17(3).
Martidis, Adam et al., Intravitreal Triamcinolone for Refractory Diabetic Macular Edema, Ophthalmology, 2002, 920-927, 109.
Maurice, David, Micropharmaceutics of the Eye, Ocular Inflammation Therapy, 1983, 97-102, 1.
McCarty, DJ, et al., Inflammatory Reaction After Intrasynovial Injection of Microcrystalline Adrenocorticosteroid Esters, Arthritis and Rheumatism, Aug. 1964, 359-367, 7(4), Grune and Stratton.
McCuen B. et al., The lack of toxicity of intravitreally administered triamcinolone acetonide, American Journal of Ophthalmology, 1981, 785-788, 91.
McGhee, Charles N.J., Locally Administered Ocular Corticosteroids Benefits and Risks, Drug Safety, 2002, 33-55, 25(1), US.
Miller, Robert et al., Degradation Rates of Oral Resorbable Implants (Polyactates and Polyglycolates): Rate Modification with Changes in PLA/PGA Copolymer Ratios, Journal of Biomedical Materials Research, 1977, 711-719, 11.
Miller, Thomas et al., Synthesis and Structure-Activity Profiles of A-Homoestranes, the Estratopones, Journal of Medical Chemistry, 1997, 3836-3841, 40.
Morita, Yasushi et al., Intravitreous Delivery of Dexamethasone Sodium m-Sulfobenzoate from Poly (DL-Lactic Acid) Implants, Biological and Pharmaceutical Bulletin, 1998, 188-190, 21(2), US.
Nauck, M. et al., Induction of vascular endothelial growth factor by platelet-activating factor and platelet-derived growth factor is downregulated by corticosteroids, American Journal of Respiratory Cell and Molecular Biology, 1997, 398-406, 16.
Nauck, Markus et al., Corticosteroids inhibit the expression of the vascular endothelial growth factor gene in Human vascular smooth muscle cells, European Journal of Pharmacology, 1998, 309-315, 341.
Nishimura et al., Isolating Triamcinolone Acetonide Particles for Intravitreal Use With a Porous Membrane Filter, Retina, 2003, 777-779, 23(6).
Oculex, Oculex Announces Positive Clinical Results for Posurdex(r) the first biodegradable ocular implant, PR Newswire, Aug. 6, 2002, 1-2.
Olsen, Timothy et al., Human Scleral Permeability: Effects of Age, Cryotherapy, Transcleral Diode Laser, and Surgical Thinning, Investigative Ophthalmology and Visual Science, 1995, 1893-1903, 36(9).
Pe'er, Jacob et al., Vascular endothelial growth factor by platelet-activating factor and platelet-derived growth factor upregulation in human central retinal vein occlusion, Ophthalmology, 1998, 412-416, 105.
Penfold, Philip et al., Exudative Macular Degeneration and Intravitreal Triamcinolone: A Pilot Study, Australian and New Zealand Journal of Ophthalmology, 1995, 293-298, 23(4).
Phillips, Calbert et al., Penetration of Timolol Eye Drops Into Human Aqueous Humour: The First Hour, British Journal of Ophthalmology, 1985, 217-218, 69.
Phillips, Tania et al., Efficacy of 0.1% Tazarotene Cream for the Treatment of Photodamage, Archives of Dermatology, Nov. 2002, 1486-1493, 138(11).
Physician'S Desk Reference, Alphagan, Product Information, 2000, 493-494, 54th Edition.
Physician'S Desk Reference, Ophthalmic Medicines, 2002, 285-294, 30th Edition.
Pribluda, Victor et al., 2-Methoxyestradiol: An Endogenous Antiangionic and Antiproliferative Drug Candidate, Cancer and Metastasis Reviews, 2000, 173-179, 19.
Quigley, Harry et al., The Mechanism of Optic Nerve Damage in Experimental Acute Intraocular Pressure Elevation, Investigative Ophthalmology and Visual Science, 1980, 505-517, 19.

(56) References Cited

OTHER PUBLICATIONS

Rao, N.A. et al., Intraocular Inflammation and Uveitis, Basic and Clinical Science Course, 1997-1998, 57-80; 102-103; 152-156, Section 9; Part 2, San Francisco: American Academy of Ophthalmology.
Rao, Venkateshwar et al., Preparation and Evaluation of Ocular Inserts Containing Norfloxacin, Turkish Journal of Medical Science, 2004, 239-246, 9.
Rechtman et al., Intravitreal triaminolone with photodynamic therapy for subfoveal choroidal neovascularisation in age related macular degeneration, British Journal of Ophthalmology, 2004, 344-347, 88.
Renfro, Lisa et al., Ocular Effects of Topical and Systemic Steroids, Dermatologic Clinics, 1992, 505-512, 10.
Roff, W.J. and Scott, J.R., Handbook of Common Polymers, latest edition, CRC Press, Cleveland, Oh.
Rogojina, Anna et al., Comparing the Use of Affymetrix to Spotted Oligonucleotide Microarrays Using Two Retinal Pigment Epithelium Cell Lines, Molecular Vision, 2003, 482-496, 9.
Roth, Daniel et al., Noninfectious Endophthalmitis Associated With Intravitreal Triamcinolone Injection, Archives of Ophthalmology, 2003, 1279-1282, 121.
Schindler, R.H. et al., The Clearance of Intravitreal Triamcinolone Acetonide, American Journal of Ophthalmology, Apr. 1982, 415-417, 93(4).
Scholes, G.N. et al., Clearance of Triamcinolone From Vitreous, Archives of Ophthalmology, 1985, 1567-1569, 103(10).
Schonfeld, David, Lumigan Found Effective in Early Phase 3, Ocular Surgery News, Mar. 2001, 35, 19(5)1.
Schuettauf, Frank et al., Effects of Anti-Glaucoma Medications on Ganglion Cell Survival: the DBA/2J Mouse Model, Vision Research, 2002, 2333-2337, 42(20).
Schumacher, Guido et al., The Physiological Estrogen Metabolite 2-Methoxyestradiol Reduced Tumor Growth and Induces Apoptosis in Human Solid Tumors, Journal of Cancer Research and Clinical Oncology, 2001, 405-410, 127.
Schwartz, Bernard, The Response of Ocular Pressure to Corticosteroids, Ophthamology Clinics of North America, 1966, 929-989, 6.
Siebold, Earlene et al., Esterified Prostaglandin Shows 'Potent' Promise, Ocular Surgery News, Feb. 1, 1989, pp. 3, 59, 7(3).
Skalka, Harold et al., Effect of Corticosteroids on Cataract Formation, Archives of Ophthalmology, 1980, 1773-1777, 98.
Smith, Thomas et al., Sustained-Release Subconjunctival 5-Fluorouracil, Ophthalmic Surgery and Laser, Sep. 1996, 763-767, 27(9).
Starr, Michael, Further Studies on the Effects of Prostaglandin on Intraocular Pressure in the Rabbit, Experimental Eye Research, 1971, 170-177, 11.

Streilein, J. Wayne et al., Ocular Immune Privilege: Therapeutic Opportunities From an Experiment of Nature, Nature Reviews Immunology, Nov. 2003, 879-889, 3.
Survey of Ophthalmology, May-Jun. 2002, p. 295, vol. 47, Issue 3.
Sutter, F.K.P. et al., Pseudo-Endophthalmitis After Intravitreal Injection of Triamcinolone, British Journal of Ophthalmology, 2003, 972-974, 87.
Tan, D.T.H. et al., Randomized Clinical Trial of a New Dexamethasone Delivery System (Surodex) for Treatment of Post-Cataract Surgery Inflammation, Ophthalmology, Feb. 1999, 223-231, 106(2), US.
Tazarotene, Drugs of the Future, Dermatologic Drugs, 2003, 208-209, 28(2).
Tazorac Product Information Sheet, Allergan, Inc., 2004, 1-8.
The Merck Index, Hydrocortisone, The Merck Index, 2009, 3 Pages, US.
Tracy, M.A. et al., Factors Affecting the Degradation Rate of Poly(lactide-co-glycolide) Microspheres in Vivo and in Vitro, Biomaterials, 1999, 1057-1062, 20.
U.S. Appl. No. 60/567,423, filed Apr. 30, 2004.
U.S. Appl. No. 60/587,092, filed Jul. 12, 2004.
United States Pharmacopeia, The National Formulary, USP24, 2000, 1941-1951, 19.
Watson, Peter et al., A Six-month, Randomized, Double-masked Study Comparing Latanoprost with Timolol in Open-Angle Glaucoma and Ocular Hypertension, Ophthalmology, 1996, 126-137, 103.
Wheeler, Larry et al., Role of Alpha-2-Agonists in Neuroprotection, Survey of Ophthalmology, 2003, S47-S51, 48(Suppl 1).
Wheeler, Larry, Experimental Study of Agents with Potential Neuroprotective Properties, Acta Ophthalmologica Scandinavica, 1999, 27-28, 77(220).
Woldemussie, Elizabeth et al., Neuroprotection Effects of Memantine in Different Retinal Injury Models in Rats, Journal of Glaucoma, 2002, 474-480, 11(6).
Woldemussie, Elizabeth, Neuroprotection of Retinal Ganglion Cells in Experimental Models of Glaucoma, Minerva Ophthalmology, 2000, 71-78, 42(2).
Woodward, David et al., AGN 192024 (LumiganR): A Synthetic Prostamide Analog that Lowers Primate Intraocular Pressure by Virtue of Its Inherent Pharmacological Activity, ARVO, 2002, 1 page (Abstract), 43.
Woodward, David et al., The Pharmacology of Bimatoprost (LumiganTM), Survey of Ophthalmology, May 2001, 5337-S345, 45(Suppl 4).
Yeung, Chi Kong et al., Cytotoxicity of Triamcinolone on Cultured Human Retinal Pigment Epithelial Cells: Comparison with Dexamethasone and Hydrocortisone, Japanese Journal of Opthamology, 2004, 236-242, 48.
Zhou, Tianhong et al., Development of a Multiple-Drug Delivery Implant for Intraocular Management of Proliferative Vitreoretinopathy, Journal of Controlled Release, 1998, 281-295, 55, US.

\* cited by examiner

COMPOSITIONS AND METHODS FOR LOCALIZED THERAPY OF THE EYE

CROSS REFERENCE TO RELATED APPLICATIONS

This application is a continuation of copending U.S. patent application Ser. No. 13/367,070, filed Feb. 6, 2012, which is a continuation of U.S. patent application Ser. No. 11/039,192, filed Jan. 19, 2005, now abandoned, which claims the benefit of U.S. Provisional Application 60/537,620, filed Jan. 20, 2004, the entire contents of which are hereby incorporated by reference.

The present invention relates to compositions that are delivered to the posterior segment of an eye of a human or animal. More particularly, the invention relates to compositions including one or more poorly soluble therapeutic agents present in particles that are sized and/or distributed to provide localized therapy to the posterior of an eye.

Corticosteroids, among other agents, are utilized to treat a wide variety of ophthalmic diseases that affect the posterior segment of an eye. Examples of some diseases treated with corticosteroids includes: central retinal vein occlusion (CRVO), branch retinal vein occlusion (BRVO), choroidal macular edema (CME), diabetic macular edema (DME), diabetic macular retinopathy, uveitis, telangitis, and age related macular degeneration (ARMD) as well as other diseases of the posterior segment.

In treating ocular diseases or disorders, steroids can be administered systemically, however systemic administration of steroids is often associated with side effects that are generally too great for ophthalmic use. Thus, topical, suprachoroidal, subconjunctival, retrobulbar, and intravitreal administration have also been studied.

Although direct intravitreal administration of current therapeutic agents may address some problems associated with systemic administration, intravitreal administration of existing ophthalmic compositions may result in ocular hypertension, as well as steroid glaucoma and posterior subcapsular cataracts, when steroids are administered. For example, approximately 25% of patients receiving intraocular corticosteroid therapy will experience an elevation of intraocular pressure (IOP) with about 10% of the patients having an IOP as high as 28 to 30 mm Hg. The IOP is thought to be due to increased outflow resistance resulting from changes in the trabecular meshwork cells. The ocular hypertension is particularly common in "steroid responders".

In addition, the formulation currently used in clinical practice contains excipients that are toxic to the internal ocular structures. For example, Kenalog®, is a commercially available formulation of triamcinolone acetonide containing such undesirable excipients. Kenalog has been shown to cause ERG changes in rabbits and its preservative, benzyl alcohol, has been implicated in such changes.

The desired site of action for therapeutic agents administered to the posterior segment of an eye generally, and corticosteroids in particular, is the retinal pigmented epithelium (RPE). The RPE is a single cell layer responsible for maintenance of the blood-retinal barrier as well as subretinal fluid volume and composition. The cells of the RPE comprise the outer blood retinal barrier and are joined by zonulae occludente tight junctions. As such, permeation of compounds into the RPE is quite limited. Thus, regardless of the administration route, penetration of a therapeutic agent through the outer blood-retinal barrier is limited. To overcome these limitations extremely high and potentially toxic doses of drugs are frequently used.

In certain situations, drugs are administered by controlled or sustained release technologies to attempt to increase their duration of action or reduce the toxicity of transient high general concentrations.

Some poorly soluble therapeutic agents, such as corticosteroids, however, are well tolerated locally and have a prolonged duration of action by virtue of their own intrinsic dissolution rates. For example, triamcinolone acetonide has been successfully administered by direct intravitreal injection do to its slow dissolution rate and tolerability. Unfortunately, side effects from the existing triamcinolone acetonide formulation include endophthalmitis as well as retinal toxicity from the benzyl alcohol preservative. Glaucoma and cataract are also observed.

Reducing the lens concentration of a corticosteroid may help mitigate the cataractogenic potential of these drugs. Additionally, reducing the anterior segment concentration of the corticosteroids relative to the posterior concentrations may reduce the chance of elevating the TIGR (MYOC, GLC1A) gene activity in the trabecular meshwork thought to be associated with steroid induced glaucoma.

Thus, there is a need for new compositions for injection into the posterior segments of eyes of humans or animals and methods for providing desired therapeutic effects in the posterior segments of eyes of humans or animals.

SUMMARY OF THE INVENTION

New compositions and methods for treating posterior segments of eyes of humans or animals have been discovered. The present compositions are highly suitable for intravitreal administration into the posterior segments of eyes and provide localized therapeutic effects to the posterior portion of an eye and reduced adverse side-effects to anterior structures or tissues of an eye.

In one broad embodiment, the present compositions include a therapeutic component that includes a therapeutic agent in the form of or present in particles. The particles are sized to form one or more concentrated regions of the therapeutic agent in the RPE of an eye of a human or animal patient. The particles are sized to be phagocytized or pinocytized by the cells of the RPE, thereby circumventing the blood-retinal barrier to treat ocular diseases or disorders. In certain embodiments, the therapeutic agent is a steroid, such as a corticosteroid.

The particles may include a combination of a poorly soluble therapeutic agent and an ophthalmically acceptable polymer component. For example, a composition may include a triamcinolone acetonide in combination with a particulate polymer, such as a bead. In another embodiment, the therapeutic agent may be formed as particles in a vehicle suspension or carrier. For example, and in at least one embodiment, the particles comprise a combination of a corticosteroid and a polysaccharide, such as hyaluronic acid. In other words, the particles may include particles of a corticosteroid that have been stabilized with hyaluronic acid. The particles may have a size less than about 3000 nanometers, and in certain embodiments, the particles may have a size less than about 200 nanometers.

In another embodiment, an ophthalmically acceptable composition comprises a population of particles of triamcinolone acetonide having an effective average particle size less than about 3000 nanometers. In one specific embodiment, the particles are formed by subjecting or exposing the triamcinolone acetonide to hyaluronic acid.

In an additional embodiment, a population of particles including triamcinolone acetonide is provided. The population of particles has an effective average particle size less than about 3000 nanometers. The particles may be provided in a liquid vehicle or carrier component before administration to an eye. One example of such a carrier component includes hyaluronic acid. The particles and carrier component may also be provided in a dispensing apparatus prior to administration to an eye.

Methods of treating patients are also disclosed and are included within the scope of the present invention. In general, such methods comprise administering, e.g. injecting a particulate therapeutic agent-containing composition, for example, a composition in accordance with the present intention, to a posterior segment of an eye of a human or animal. Such administering is effective in providing a desired therapeutic effect. The administering step advantageously comprises at least one of intravitreal injecting, subconjunctival injecting, sub-tenon injecting, retrobulbar injecting, suprachoroidal injecting and the like.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

These and other aspects and advantages of the present invention are apparent in the following detailed description, examples and claims.

DETAILED DESCRIPTION

The present invention involves compositions, such as ophthalmic compositions, that provide therapy to a patient. In accordance with the disclosure herein, compositions are disclosed that are useful for placement, preferably by injection, into a posterior segment of an eye of a human or animal, and preferably a living human or animal. Such compositions in the posterior, e.g., vitreous, of the eye are therapeutically effective against one or more conditions and/or diseases of the posterior of the eye, and/or one or more symptoms of such conditions and/or diseases of the posterior of the eye, among other things.

In general, the present compositions comprise a therapeutic component which comprises a poorly soluble therapeutic agent in the form of or present in small particles. The particles typically have a size, for example, a length, a width, a diameter, a cross-sectional area, a surface area, or a volume, on the order of micrometers or nanometers. The therapeutic agent may be shaped or otherwise manufactured as particles, or may be coupled to particles of other materials. The particles including the therapeutic agent have a size that is effective to form concentrated regions of the therapeutic agent in the retinal pigmented epithelium (RPE) of an eye to which the composition or particles are administered. The concentrated regions of the therapeutic agent are effective to provide a desired therapeutic effect to the human or animal, such as a therapeutic effect to a posterior portion of the eye.

In comparison, existing pharmaceutical compositions which are used to provide ocular therapy contain a therapeutic agent which does not form concentrated regions of the therapeutic agent in the RPE of an eye. Thus, the ophthalmically-acceptable pharmaceutical compositions disclosed herein are effective to provide more localized drug delivery to a posterior portion of an eye of a patient relative to existing compositions containing a substantially identical therapeutic agent.

The concentrated regions of the poorly soluble therapeutic agent are localized to the posterior portion of an eye of a patient, such as the RPE. In certain aspects, the particles are sized to form one or more discrete regions of concentrated therapeutic agent in the RPE relative to other regions of the RPE. In other words, administration of the particles disclosed herein to a posterior portion of an eye of a patient may result in one or more areas of the RPE having a relatively higher concentration of therapeutic agent, and one or more regions having a relatively lower concentration of therapeutic agent.

The concentrated regions may be understood to be or to function as RPE depots of the therapeutic agent. By sizing the particles appropriately to form concentrated regions of the therapeutic agent, the delivery of the therapeutic agent to the patient can be prolonged for periods of time, such as days, weeks, or months. Thus, the particles disclosed herein may be effective to provide extended-release of the therapeutic agent into the posterior portion of the eye. The release rate may be substantially continuous occurring by relatively passive biological and/or chemical processes, or the release rate may be discontinuous, for example pulsatile or periodic, to achieve a desired therapeutic effect.

In certain embodiments, the composition comprises a therapeutically effective amount of the therapeutic agent before the composition is administered to an eye. In other embodiments, the composition may comprise a sub-therapeutically effective amount of the therapeutic agent before it is administered to the eye, and the concentrated regions of the therapeutic agent are formed to have a therapeutically effective amount of the therapeutic agent. In other words, the concentrated regions may have a concentration of the therapeutic agent that is greater than the concentration of the therapeutic agent of the composition before the composition is administered to an eye.

The concentrated regions may also have a concentration of the therapeutic agent that is greater relative to the concentration of the therapeutic agent in the composition when the composition is administered to the eye, for example, the concentration of the therapeutic agent that is present in the vitreous of the eye.

In addition, or alternatively, the concentrated regions may have a concentration of particles that is greater than the concentration of the particles in the composition, either before administration to the eye, or after administration to the eye and as present in the vitreous of the eye. The concentrated regions of the therapeutic agent may be effective to provide an enhanced therapeutic effect relative to substantially identical compositions in which the therapeutic agent is not provided as particles, or as particles having the same or similar sizes to that disclosed herein.

For example, the therapeutic agent may be present in the composition in an amount of at least about 10 mg per ml of the composition. One advantage of certain embodiments of the present invention is the effective ability of the present compositions to include relatively smaller amounts or concentrations of the therapeutic agent in the composition while obtaining a relatively larger amount or concentration of the therapeutic agent at a target site, such as the RPE. Thus, the therapeutic agent may be present in the present compositions in an amount in the range of about 1% or less to about 5% or about 10% or about 20% or about 25% or about 30% or more (w/v) of the composition. In accordance with the disclosure herein, reduced amounts of the composition may be required to be placed or injected into the posterior segment of the eye in order to provide the same amount or more therapeutic agent in the posterior segment of the eye relative to existing compositions, such as Kenalog®-40.

The particles including the therapeutic agent are sized so that the particles are distributed in the composition when administered to the eye to reduce toxicity associated with the therapeutic agent in the anterior tissues of the eye, such as the lens, the iris-ciliary body, the aqueous humor, and the like. Thus, by sizing the particles appropriately, a targeted delivery of the therapeutic agent can be obtained that is effective to reduce, and preferably prevent, toxicity to anterior structures of the eye.

Examples of therapeutic agents that can be formed as particles, as disclosed herein, include, without limitation, any conventional poorly soluble ophthalmic therapeutic agent. Such therapeutic agents advantageously have a limited solubility in a fluid, such as water, for example, at 25° C. or at 37° C. For example, the therapeutic agent preferably has a solubility in water at 25° C. or at 37° C. of less than 10 mg/ml. Of course, the therapeutic agent should be ophthalmically acceptable, that is, should have substantially no significant or undue detrimental effect of the eye structures or tissues.

For example, therapeutic agents may include retinoids, prostaglandins, tyrosine kinase inhibitors, adrenoreceptor agonists or antagonists, dopaminergic agonists, cholinergic agonists, carbonic anhydrase inhibitors, guanylate cyclase activators, cannabinoids, endothelin, adenosine agonists, antiangiogenic compounds, angiostatic compounds, and neuroprotectants. When a therapeutic agent is not poorly soluble, it may be physically or chemically modified to become poorly soluble using conventional methods known to persons of ordinary skill in the art.

More specifically, the therapeutic agent may include non-steroidal anti-inflammants, analgesics, or antipyretics, antihistamines, antibiotics, beta blockers, steroids, such as corticosteroids, anti-neoplastic agents, immunosuppressive agents, antiviral agents, and antioxidants.

Non-limiting examples of non-steroidal anti-inflammants, analgesics, and antipyretics, include aspirin, acetaminophen, ibuprofen, naproxen, diclofenac, etodolac, fenoprofen, indomethacin, ketoprofen, oxaprozin, piroxicam, sulindac, diflunisal, mefenamic acid, and derivatives thereof.

As used herein, the term "derivative" refers to any substance which is sufficiently structurally similar to the material which it is identified as a derivative so as to have substantially similar functionality or activity, for example, therapeutic effectiveness, as the material when the substance is used in place of the material. The functionality of any derivative disclosed herein may be determined using conventional routine methods well known to persons of ordinary skill in the art.

Examples of antihistamines include, and are not limited to, loratadine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimeprazine doxylamine, pheniramine, pyrilamine, chlorcyclizine, thonzylamine, and derivatives thereof.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, and derivatives thereof.

Examples of beta blockers include acebutolol, atenolol, labetalol, metoprolol, propranolol, and derivatives thereof.

Examples of corticosteroids include cortisone, prednisolone, triamcinolone, fluorometholone, dexamethasone, medrysone, loteprednol, fluazacort, hydrocortisone, prednisone triamcinolone, betamethasone, prednisone, methylprednisolone, triamcinolone acetonide, triamcinolone hexacetonide, paramethasone acetate, diflorasone, fluocinolone and fluocinonide, derivatives thereof, and mixtures thereof.

Examples of antineoplastic agents include adriamycin, cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppressive agents include cyclosporine, azathioprine, tacrolimus, and derivatives thereof.

Examples of antiviral agents include interferon gamma, zidovudine, amantadine hydrochloride, ribavirin, acyclovir, valacyclovir, dideoxycytidine, and derivatives thereof.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryptoxanthin, astaxanthin, lycopene, N-acetyl-cysteine, carnosine, gamma-glutamyl-cysteine, quercetin, lactoferrin, dihydrolipoic acid, citrate, *Ginkgo Biloba* extract, tea catechins, bilberry extract, vitamins E or esters of vitamin E, retinyl palmitate, and derivatives thereof.

Other therapeutic agents include squalamine, carbonic anhydrase inhibitors, alpha agonists, prostamides, prostaglandins, antiparasitics, antifungals, and derivatives thereof.

In a preferred embodiment of the invention, the therapeutically active agent or therapeutic agent comprises a retinoid, a prostaglandin, a tyrosine kinase inhibitor, a glucocorticoid, an androgenic steroid, an estrogenic steroid, or a non-estrogenic steroid, an intracellular adhesion molecule inhibitor, or an alpha-2-adrenergic receptor agonist. In one specific embodiment, the therapeutic agent is triamcinolone acetonide.

The therapeutic agent of the present compositions may include any or all salts and prodrugs or precursors of the therapeutic agents, including those specifically identified herein.

In certain embodiments, the therapeutic component of the composition may comprise particles including more than one therapeutic agent. In other words, the therapeutic component of the composition may include a first therapeutic agent, and a second therapeutic agent, or a combination of therapeutic agents. Examples of therapeutic agents include those identified above in any combination. One or more of the therapeutic agents in such compositions may be formed as or present in particles, as disclosed herein.

The compositions disclosed herein may include a therapeutic component that comprises, consists essentially of, or consists of, a population of particles including a therapeutic agent. Each of the particles have a size. When the particles are grouped to define a population of particles, the population may have an effective average particle size that corresponds to the average size of the particles of that population. The size of the particles may be uniformly distributed in any given population. For example, the size of particles in a population may be symmetrically distributed about the mean size of the particles. Or, the size of the particles may be distributed asymmetrically. For example, a population of particles may have an effective average particle size that is skewed away from the median particle size for a population of particles.

In certain embodiments, the compositions comprise a population of particles including a first therapeutic agent and a population of particles including a second therapeutic agent. Thus, in at least one embodiment, a composition comprises a population of particles having an effective average particle size that is effective to form concentrated regions of the therapeutic agent. In certain embodiments, a population of particles has an average size effective to promote phagocytosis of the particles by RPE cells. In other embodiments, a population of particles has an average size effective to promote pinocytosis by RPE cells. The compositions disclosed herein may thus have a population of a predetermined number of particles with a desired or predetermined size. This may provide enhanced therapeutic effects relative to existing compositions that do not have populations of a predetermined number of particles of a specific size. For example, some compositions may include "fines" of therapeutic agent particles. Fines, as used herein, may be understood to be particles that are randomly formed during the manufacture of the particles. Fines may be relatively small, but because they occur randomly, they do not provide a desired therapeutic effect.

In certain embodiments, such as embodiments in which the particles promote phagocytosis, the particles may have an average size of about 3000 nanometers. Usually, the particles will have an effective average size less than about 3000 nanometers. In more specific embodiments, the particles may have an effective average particle size about an order of magnitude smaller than 3000 nanometers. For example, the particles may have an effective average particle size of less than about 500 nanometers. In further embodiments, the particles may have an effective average particle size of less than about 400 nanometers, and in still further embodiments, a size less than about 200 nanometers. Reducing the size of the particles may be effective to cause the particles to form concentrated regions by pinocytosis mechanisms as compared to phagocytosis mechanisms.

In addition, a composition may include a therapeutic component with more than one population of particles, each population having a different effective average particle size. In one specific embodiment, the therapeutic component may comprise a first population of particles including a therapeutic agent having an effective average particle size of less than about 200 nanometers, a second population of particles having an effective average particle size in a range of about 200 nanometers to about 400 nanometers, and a third population of particles having an effective average particle size in a range of about 400 nanometers to about 3000 nanometers.

In at least one embodiment, the particles of the composition may comprise, consist essentially of, or consist of, a therapeutic agent and a polymer suitable for administration to the posterior segment of an eye. The polymer in combination with the therapeutic agent may be understood to be a polymeric component. In some embodiments, the particles comprise materials other than D,L-polylactide (PLA) or latex (carboxylate modified polystyrene beads). In certain embodiments, the polymer component may comprise a polysaccharide. For example, the polymer component may comprise a mucopolysaccharide. In at least one specific embodiment, the polymer component is hyaluronic acid.

However, in additional embodiments, the polymeric component may comprise any polymeric material useful in a body of a mammal, whether derived from a natural source or synthetic. Some additional examples of useful polymeric materials for the purposes of this invention include carbohydrate based polymers such as methylcellulose, carboxymethylcellulose, hydroxymethylcellulose hydroxypropylcellulose, hydroxyethylcellulose, ethyl cellulose, dextrin, cyclodextrins, alginate, hyaluronic acid and chitosan, protein based polymers such as gelatin, collagen and glycoproteins, hydroxy acid polyesters such as polylactide-coglycolide (PLGA), polylactic acid (PLA), polyglycolide, polyhydroxybutyric acid, polycaprolactone, polyvalerolactone, polyphosphazene, and polyorthoesters. Polymers can also be crosslinked, blended or used as copolymers in the invention. Other polymer carriers include albumin, polyanhydrides, polyethylene glycols, polyvinyl polyhydroxyalkyl methacrylates, pyrrolidone and polyvinyl alcohol.

Some examples of non-erodible polymers include silicone, polycarbonates, polyvinyl chlorides, polyamides, polysulfones, polyvinyl acetates, polyurethane, ethylvinyl acetate derivatives, acrylic resins, crosslinked polyvinyl alcohol and crosslinked polyvinylpyrrolidone, polystyrene and cellulose acetate derivatives.

These additional polymeric materials may be useful with any of the therapeutic agents. For example, particles of PLA or PLGA may be coupled to triamcinolone acetonide, in one embodiment.

The particles of the therapeutic agent or agents may also be combined with a pharmaceutically acceptable vehicle component in the manufacture of a composition. In other words, a composition, as disclosed herein, may comprise a therapeutic component, as discussed above, and an effective amount of a pharmaceutically acceptable vehicle component. In at least one embodiment, the vehicle component is aqueous-based. For example, the composition may comprise water.

In certain embodiments, the vehicle component may also include an effective amount of at least one of a viscosity inducing component, a resuspension component, a preservative component, a tonicity component and a buffer component. In some embodiments, the compositions disclosed herein include no added preservative component. In other embodiments, a composition may include an added preservative component. In addition, the composition may be included with no resuspension component.

The aqueous vehicle component is advantageously ophthalmically acceptable and may also include one or more conventional excipients useful in ophthalmic compositions.

The present compositions preferably include a major amount of liquid water. The present compositions may be, and are preferably, sterile, for example, prior to being used in the eye.

The present compositions preferably include at least one buffer component in an amount effective to control the pH of the composition and/or at least one tonicity component in an amount effective to control the tonicity or osmolality of the compositions. More preferably, the present compositions include both a buffer component and a tonicity component.

The buffer component and tonicity component may be chosen from those which are conventional and well known in the ophthalmic art.

Examples of such buffer components include, but are not limited to, acetate buffers, citrate buffers, phosphate buffers, borate buffers and the like and mixtures thereof. Phosphate buffers are particularly useful. Useful tonicity components include, but are not limited to, salts, particularly sodium chloride, potassium chloride, any other suitable ophthalmically acceptably tonicity component and mixtures thereof.

The amount of buffer component employed preferably is sufficient to maintain the pH of the composition in a range of about 6 to about 8, more preferably about 7 to about 7.5. The amount of tonicity component employed preferably is sufficient to provide an osmolality to the present compositions in a range of about 200 to about 400, more preferably about 250 to about 350, mOsmol/kg respectively. Advantageously, the present compositions are substantially isotonic.

The present compositions may include one or more other components in amounts effective to provide one or more useful properties and/or benefits to the present compositions. For example, although the present compositions may be substantially free of added preservative components, in other embodiments, the present compositions include effective amounts of preservative components, preferably such components which are more compatible with or friendly to the tissue in the posterior segment of the eye into which the composition is placed than benzyl alcohol. Examples of such preservative components include, without limitation, benzalkonium, chloride, methyl and ethyl parabens, hexetidine, chlorite components, such as stabilized chlorine dioxide, metal chlorites and the like, other ophthalmically acceptable preservatives and the like and mixtures thereof. The concentration of the preservative component, if any, in the present compositions is a concentration effective to preserve the composition, and is often in a range of about 0.00001% to about 0.05% or about 0.1% (w/v) of the composition.

In addition, the present composition may include an effective amount of resuspension component effective to facilitate the suspension or resuspension of the therapeutic component particles in the present compositions. As noted above, in certain embodiments, the present compositions are free of added resuspension components. In other embodiments of the present compositions effective amounts of resuspension components are employed, for example, to provide an added degree of insurance that the therapeutic component particles remain in suspension, as desired and/or can be relatively easily resuspended in the present compositions, such resuspension be desired. Advantageously, the resuspension component employed in accordance with the present invention, if any, is chosen to be more compatible with or friendly to the tissue in the posterior segment of the eye into which the composition is placed then polysorbate 80.

Any suitable resuspension component may be employed in accordance with the present invention. Examples of such resuspension components include, without limitation, surfactants such as poloxamers, for example, sold under the trademark Pluronic®; tyloxapol; sarcosinates; polyethoxylated castor oils, other surfactants and the like and mixtures thereof.

One very useful class of resuspension components are those selected from vitamin derivatives. Although such materials have been previously suggested for use as surfactants in ophthalmic compositions, they have been found to be effective in the present compositions as resuspension components. Examples of useful vitamin derivatives include, without limitation, Vitamin E tocopheryl polyethylene glycol succinates, such as Vitamin E tocopheryl polyethylene glycol 1000 succinate (Vitamin E TPGS). Other useful vitamin derivatives include, again without limitation, Vitamin E tocopheryl polyethylene glycol succinimides, such as Vitamin E tocopheryl polyethylene glycol 1000 succinimide (Vitamin E TPGSA) wherein the ester bond between polyethylene glycol and succinic acid is replaced by an amide group.

The presently useful resuspension components are present, if at all, in the compositions in accordance with the present invention in an amount effective to facilitate suspending the particles in the present compositions, for example, during manufacture of the compositions or thereafter. The specific amount of resuspension component employed may vary over a wide range depending, for example, on the specific resuspension component being employed, the specific composition in which the resuspension component is being employed and the like factors. Suitable concentrations of the resuspension component, if any, in the present compositions are often in a range of about 0.01% to about 5%, for example, about 0.02% or about 0.05% to about 1.0% (w/v) of the composition.

The compositions disclosed herein may include a viscosity inducing component in an amount effective in providing an increased viscosity to the composition relative to an identical composition without the viscosity inducing component. The viscosity inducing component may comprise at least one viscoelastic agent.

Any suitable viscosity inducing component, for example, ophthalmically acceptable viscosity inducing component, may be employed in accordance with the present invention. Many such viscosity inducing components have been proposed and/or used in ophthalmic compositions used on or in the eye. The viscosity inducing component is present in an amount effective in providing the desired viscosity to the composition. Advantageously, the viscosity inducing component is present in an amount in a range of about 0.5% or about 1.0% to about 5% or about 10% or about 20% (w/v) of the composition. The specific amount of the viscosity inducing component employed depends upon a number of factors including, for example and without limitation, the specific viscosity inducing component being employed, the molecular weight of the viscosity inducing component being employed, the viscosity desired for the present composition being produced and/or used and the like factors. The viscosity inducing component is chosen to provide at least one advantage, and preferably multiple advantages, to the present compositions, for example, in terms of each of injectability into the posterior segment of the eye, viscosity, sustainability of the corticosteroid component particles in suspension, for example, in substantially uniform suspension, for a prolonged period of time without resuspension processing, compatibility with the tissues in the posterior segment of the eye into which the composition is to be placed and the like advantages. More preferably, the selected viscosity inducing component is effective to provide two or more of the above-noted benefits, and still more preferably to provide all of the above-noted benefits.

The viscosity inducing component preferably comprises a polymeric component and/or at least one viscoelastic agent, such as those materials which are useful in ophthalmic surgical procedures.

Examples of useful viscosity inducing components include, but are not limited to, hyaluronic acid, carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures thereof.

The molecular weight of the presently useful viscosity inducing components may be in a range of about 10,000 Daltons or less to about 2 million Daltons or more. In one particularly useful embodiment, the molecular weight of the viscosity inducing component is in a range of about 100,000 Daltons or about 200,000 Daltons to about 1 million Daltons or about 1.5 million Daltons. Again, the molecular weight of the viscosity inducing component useful in accordance with the present invention, may vary over a substantial range based on the type of viscosity inducing component employed, and the desired final viscosity of the present composition in question, as well as, possibly one or more other factors.

In one very useful embodiment, a viscosity inducing component is a hyaluronate component, for example, a metal hyaluronate component, preferably selected from alkali metal hyaluronates, alkaline earth metal hyaluronates and mixtures thereof, and still more preferably selected from sodium hyaluronates, and mixtures thereof. The molecular weight of such hyaluronate component preferably is in a range of about 50,000 Daltons or about 100,000 Daltons to about 1.3 million Daltons or about 2 million Daltons. In one embodiment, the present compositions include a hyaluronate component in an amount in a range about 0.05% to about 0.5% (w/v). In a further useful embodiment, the hyaluronate component is present in an amount in a range of about 1% to about 4% (w/v) of the composition. In this latter case, the very high polymer viscosity forms a gel that slows particle sedimentation rate to the extent that often no resuspension processing is necessary over the estimated shelf life, for example, at least about 2 years, of the composition. Such a composition may be marketed in pre-filled syringes since the gel cannot be easily removed by a needle and syringe from a bulk container.

In at least one embodiment, the viscosity inducing component is selected from the group consisting of hyaluronic acid, carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures thereof. In certain embodiments, the viscosity inducing component comprises a hyaluronate component, such as a sodium hyaluronate. Advantageously, it has been discovered that compositions which include a therapeutic component comprising a therapeutic agent in the form of particles fabricated from a hyaluronic acid component provide an effective viscosity to the composition as well as the desired formation of concentrated regions of the therapeutic agent.

In at least one embodiment, an ophthalmically acceptable composition comprises a population of particles of triamcinolone acetonide having an effective average particle size less than about 3000 nanometers. As discussed herein, when a pinocytotic mechanism is desired for the formation of concentrated regions of the therapeutic agent, the composition may have at least a major portion of the population of particles with a size less than about 500 nanometers.

In at least one other embodiment of the invention, a population of particles of triamcinolone acetonide has an effective average particle size less than about 3000 nanometers. For example, the population of particles may have an effective average particle size less than about 500 nanometers. In at least one embodiment, the population of particles has an effective average particle size of between about 200 and about 400 nanometers.

The population of particles of triamcinolone acetonide may be provided in a liquid carrier component, and preferably, an ophthalmically acceptable liquid carrier component. One example of a liquid carrier component may include hyaluronic acid. The combination of the particles and the liquid carrier component may be provided in a container, such as a vial and/or a dispensing apparatus. For example, when the population of particles is administered to a posterior segment of an eye of a patient, the population may be provided in a syringe that is configured to administer the particles to an eye, and preferably, to a posterior segment of an eye, as discussed herein.

In at least one embodiment, the particles comprise a combination of triamcinolone acetonide and hyaluronic acid. The hyaluronic acid is believed to stabilize the particles of triamcinolone acetonide. The particles have a size, such as a width, a length, a diameter, an area, or a volume, effective to facilitate transfer of the particles into the RPE when the particles are administered to an eye.

In at least one other embodiment of the invention, a poorly soluble steroid, such as a corticosteroid, is provided as small particles. The particles preferably have an effective average particle size less than about 3000 nanometers, preferably less than about 400 nanometers, and more preferably, less than about 200 nanometers. The steroid preferably has a solubility of less than about 10 mg/mL. In at least one embodiment, the poorly soluble steroid is triamcinolone acetonide. The particles may be formed by mixing the poorly soluble steroid with a hyaluronate component. Stabilization of the particles may be obtained by one or more surface modifications of the steroid with hyaluronic acid or sodium hyaluronate.

The particles may be provided in a pharmaceutical composition, such as compositions disclosed herein. In at least one embodiment, a composition comprises a first population of particles having a size less than 200 nanometers, a second population of particles having an effective average particle size between about 200 nanometers and about 400 nanometers, and a third population of particles having an effective average particle size between about 400 nanometers and about 3000 nanometers. In additional embodiments, a composition may have only two populations of particles with different effective average particle sizes. Such compositions are substantially free, and preferably are entirely free, of fines of the therapeutic agent, as discussed herein.

The particles of the therapeutic agent disclosed herein, including triamcinolone acetonide, may be manufactured by subjecting a composition, which may not necessarily be an ophthalmic composition, of relatively large particles of the therapeutic agent and a polymeric component acceptable for administration into a posterior segment of an eye of a patient to conditions that are effective to reduce the relatively large particles to smaller particles having an effective average particle size that is effective to form concentrated regions of the therapeutic agent when placed in an eye. For example, the particles may be reduced to about 3000 nanometers or less in size. The polymeric component may be present in an amount effective in stabilizing the smaller particles in the product composition.

In at least one embodiment, the product composition is subjected to a milling step. For example, the particles may be exposed to a ball mill. As one example, hyaluronic acid can be added to particles of the therapeutic agent in an amount from about 10% to about 200% of the active therapeutic agent on a weight basis. Hyaluronic acid may be added in the form of an aqueous solution. The therapeutic agent may then be milled in the hyaluronic acid solution until the mean average particle size equals the desired range.

The particles may be sorted into different populations according to size differences. For example, the particles may be sorted by passing the particles through a series of filters having a series of openings of different sizes allowing progressively larger particles to be separated from smaller particles.

In certain embodiments, the particles may be prepared using methods such as those disclosed in U.S. Pat. Nos. 6,387,409; 5,565,188; and/or 5,552,160, the contents of all of which are hereby incorporated by reference.

Compositions can be prepared using suitable blending/processing techniques or techniques, for example, one or more conventional blending techniques. The preparation processing should be chosen to provide the present compositions in forms which are useful for placement or injection into the posterior segments of eyes of humans or animals. In one embodiment a concentrated therapeutic component dispersion is made by combining therapeutic agent in the form of particles, as discussed herein, with water and the excipients to be included in the final ophthalmic composition. The ingredients may be mixed to disperse the therapeutic component and then may be autoclaved.

A composition including particles, such as the particles described above, may be administered to a patient to provide a treatment to a patient. For example, the composition may be administered to a human or animal patient to treat an ocular condition or disease.

Among the diseases/conditions which can be treated or addressed in accordance with the present invention include, without limitation, the following:

MACULOPATHIES/RETINAL DEGENERATION: Non-Exudative Age Related Macular Degeneration (ARMD), Exudative Age Related Macular Degeneration (ARMD), Choroidal Neovascularization, Diabetic Retinopathy, Acute Macular Neuroretinopathy, Central Serous Chorioretinopathy, Cystoid Macular Edema, Diabetic Macular Edema.

UVEITIS/RETINITIS/CHOROIDITIS: Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome.

VASCULAR DISEASES/EXUDATIVE DISEASES: Retinal Arterial Occlusive Disease, Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angiitis, Sickle Cell Retinopathy and other Hemoglobinopathies, Angioid Streaks, Familial Exudative Vitreoretinopathy, Eales Disease.

TRAUMATIC/SURGICAL: Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy.

PROLIFERATIVE DISORDERS: Proliferative Vitreal Retinopathy and Epiretinal Membranes, Proliferative Diabetic Retinopathy.

INFECTIOUS DISORDERS: Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associated with HIV Infection, Uveitic Disease Associated with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis.

GENETIC DISORDERS: Retinitis Pigmentosa, Systemic Disorders with Associated Retinal Dystrophies, Congenital Stationary Night Blindness, Cone Dystrophies, Stargardt's Disease and Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum.

RETINAL TEARS/HOLES: Retinal Detachment, Macular Hole, Giant Retinal Tear.

TUMORS: Retinal Disease Associated with Tumors, Congenital Hypertrophy of the RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

MISCELLANEOUS: Punctate Inner Choroidopathy, Acute Posterior Multifocal Placoid Pigment Epitheliopathy, Myopic Retinal Degeneration, Acute Retinal Pigment Epithelitis and the like.

In one embodiment, a composition, such as the compositions disclosed herein, is administered to a posterior segment of an eye of a human or animal patient, and preferably, a living human or animal. In at least one embodiment, a composition is administered without accessing the subretinal space of the eye. For example, a method of treating a patient may include injecting the composition directly into the posterior chamber of the eye. In other embodiments, a method of treating a patient may comprise administering a composition to the patient by at least one of intravitreal injection, subconjunctival injection, sub-tenon injections, retrobulbar injection, and suprachoroidal injection.

In at least one embodiment, a method of treating a posterior segment ocular disease comprises administering a population of particles, or a composition containing such particles, as disclosed herein to a patient by at least one of intravitreal injection, subconjunctival injection, sub-tenon injection, retrobulbar injection, and suprachoroidal injection. A syringe apparatus including an appropriately sized needle, for example, a 27 gauge needle or a 30 gauge needle, can be effectively used to inject the composition with the posterior segment of an eye of a human or animal. The present methods may comprise a single injection into the posterior segment of an eye or may involve repeated injections, for example over periods of time ranging from about one week or about 1 month or about 3 months to about 6 months or about 1 year or longer.

In another aspect of the present invention, the particles and/or compositions disclosed herein are used in the manufacture of a medicament that is effective to treat one or more ocular conditions, such as an ocular condition affecting the posterior segment of an eye of a patient, and including the conditions identified herein.

While this invention has been described with respect to various specific examples and embodiments, it is to be understood that the invention is not limited thereto and that it can be variously practiced within the scope of the following claims.

What is claimed is:

1. A method of treating uveitis or retinitis in the eye of a patient in need thereof, the method comprising injecting into the subconjunctiva of an eye of a patient in need thereof a suspension composition at a frequency of once every about six months on a repeating basis, the suspension composition comprising:
   particles comprising cyclosporine and hyaluronic acid, wherein the particles have an effective average size of less than about 3000 nanometers;
   the cyclosporine in an amount of about 10% (w/v);
   hyaluronic acid in an amount in the range of 0.05% (w/v) to 0.5% (w/v);
   polysorbate 80; and
   water.

2. The method of claim 1, wherein the suspension composition further comprises mannitol.

* * * * *